(12) United States Patent
Virtanen et al.

(10) Patent No.: US 7,684,856 B2
(45) Date of Patent: Mar. 23, 2010

(54) DETECTION OF ARTIFACTS IN BIOELECTRIC SIGNALS

(75) Inventors: Juha Virtanen, Helsinki (FI); Borje Rantala, Helsinki (FI); Seppo Iikka Juhani Virtanen, Helsinki (FI)

(73) Assignee: General Electric Company, Schenectady, NY (US)

( * ) Notice: Subject to any disclaimer, the term of this patent is extended or adjusted under 35 U.S.C. 154(b) by 348 days.

(21) Appl. No.: 11/635,397

(22) Filed: Dec. 7, 2006

(65) Prior Publication Data
US 2007/0167858 A1 Jul. 19, 2007

Related U.S. Application Data

(63) Continuation-in-part of application No. 11/301,262, filed on Dec. 12, 2005, now abandoned.

(51) Int. Cl.
    *A61B 5/04* (2006.01)
(52) U.S. Cl. .................. 600/544; 600/545; 600/547
(58) Field of Classification Search ......... 600/544–546, 600/409
    See application file for complete search history.

(56) References Cited

U.S. PATENT DOCUMENTS

| | | | |
|---|---|---|---|
| 5,513,649 A * | 5/1996 | Gevins et al. | 600/544 |
| 5,704,365 A | 1/1998 | Albrecht et al. | |
| 5,807,270 A | 9/1998 | Williams | |
| 5,879,308 A | 3/1999 | Räsänen | |
| 6,625,485 B2 * | 9/2003 | Levendowski et al. | 600/544 |
| 6,658,287 B1 * | 12/2003 | Litt et al. | 600/544 |
| 7,038,601 B2 * | 5/2006 | Uutela et al. | 341/118 |
| 7,286,871 B2 * | 10/2007 | Cohen | 600/544 |

(Continued)

FOREIGN PATENT DOCUMENTS

EP 1 516 581 3/2005

(Continued)

OTHER PUBLICATIONS

*Replicability of MEG and EEG measures of the auditory N1/N1m-response*, J. Virtanen et al. Electroencephalography and Clinical Neurophysiology 108 (1998) 291-298.

(Continued)

*Primary Examiner*—Robert L Nasser
*Assistant Examiner*—Michael D'Angelo
(74) *Attorney, Agent, or Firm*—Andrus, Sceales, Starke & Sawall, LLP

(57) ABSTRACT

The invention relates to a method and apparatus for detecting artifacts in a bioelectric signal, especially in a frontal EEG signal. In order to accomplish an uncomplicated mechanism for detecting artifacts in clinical applications, an impedance signal is measured through a first electrode set attached to the skin surface in a measurement area of a patient's body, the impedance signal being indicative of the impedance of the signal path formed between individual electrodes of the set. Simultaneously with the impedance measurement, a bioelectric signal is acquired through a second electrode set also attached to the skin surface of the measurement area, and the time periods are determined during which the impedance signal fulfills at least one predetermined criterion indicative of the presence of artifact in the bioelectric signal. In one embodiment, the first and second electrode sets are formed by a common set of two electrodes.

37 Claims, 4 Drawing Sheets

U.S. PATENT DOCUMENTS

| | | |
|---|---|---|
| 2002/0138014 A1 | 9/2002 | Baura et al. |
| 2003/0006782 A1 | 1/2003 | Shambroom et al. |
| 2003/0052775 A1 | 3/2003 | Shambroom et al. |
| 2003/0088185 A1* | 5/2003 | Prass .......................... 600/546 |
| 2004/0097802 A1* | 5/2004 | Cohen ......................... 600/411 |
| 2005/0182338 A1* | 8/2005 | Huiku ......................... 600/544 |
| 2005/0203437 A1* | 9/2005 | Shambroom et al. ........ 600/547 |
| 2006/0041201 A1* | 2/2006 | Behbehani et al. .......... 600/521 |
| 2007/0038382 A1* | 2/2007 | Keenan ........................ 702/19 |

FOREIGN PATENT DOCUMENTS

| | | |
|---|---|---|
| WO | WO-98/26714 | 6/1998 |
| WO | WO-2004/075738 | 9/2004 |

OTHER PUBLICATIONS

European Search Report dated May 7, 2007.

* cited by examiner

DETECTION OF ARTIFACTS IN BIOELECTRIC SIGNALS

CROSS REFERENCE TO RELATED APPLICATION

The present application is a continuation-in-part application of U.S. patent application Ser. No. 11/301,262, filed Dec. 12, 2005, now abandoned.

FIELD OF THE INVENTION

The present invention relates generally to the detection of artifacts in bioelectric signals, especially in frontal EEG signals.

BACKGROUND OF THE INVENTION

Neuromonitoring is a subfield of clinical patient monitoring focused on measuring various aspects of brain function and on changes therein caused by neurological diseases, accidents, and drugs commonly used to induce and maintain anesthesia in an operation room or sedation in patients under critical or intensive care.

Electroencephalography (EEG) is a well-established method for assessing brain activity. When measurement electrodes are attached on the skin of the skull surface, the weak biopotential signals generated in brain cortex may be recorded and analyzed. The EEG has been in wide use for decades in basic research of the neural systems of the brain as well as in the clinical diagnosis of various central nervous system diseases and disorders.

The EEG signal represents the sum of excitatory and inhibitory potentials of large numbers of cortical pyramidal neurons, which are organized in columns. Each EEG electrode senses the average activity of several thousands of cortical pyramidal neurons.

The EEG signal is often divided into four different frequency bands: Delta (0.5-3.5 Hz), Theta (3.5-7.0 Hz), Alpha (7.0-13.0 Hz), and Beta (13.0-32.0 Hz). In an adult, Alpha waves are found during periods of wakefulness, and they may disappear entirely during sleep. Beta waves are recorded during periods of intense activation of the central nervous system. The lower frequency Theta and Delta waves reflect drowsiness and periods of deep sleep.

Surface EEG always includes various artifacts and confounding signals that hamper the analysis of the brain waves. Eye movements, eye blinks, facial muscle activity, and head movements are well-known sources of interference. During EEG review, these types of artifact may interfere with the detection and analysis of the events of interest. The methods dealing with EEG artifacts may be divided between methods that remove artifacts without considering brain activity and techniques that remove artifact by attempting to separate artifact and brain activities from each other. A straightforward approach is to discard contaminated EEG epochs from further analysis based on one or more electro-oculogram (EOG) signals indicative of ocular activity and thus of the artifact caused by eye movements. This kind of method is disclosed for example in the article Virtanen J, Ahveninen J, Ilmoniemi R J, Näätänen R and Pekkonen E: Replicability of MEG and EEG measures of the auditory N1/N1m-responses, Electroencephalography and clinical Neurophysiology, 108, 291-298, 1998. This is usually the method of choice in recordings with relatively small number of EEG channels.

Another well-known approach is the EOG subtraction method, in which the proportion of ocular contamination is estimated for each EEG channel. To obtain corrected EEG data, the EOG signals measured are scaled by the estimated proportion and the scaled EOG signals are subtracted from the original EEG signals. However, as the EOG is not only sensitive to eye artifacts but also contains brain activity, this method may render the relevant brain signals distorted.

In brain research, a large number of EEG channels may be used by placing, respectively, a large number of electrodes over multiple areas of the scalp to obtain a mapping of the potential distribution over the scalp. In these applications, the additional degrees of freedom provided by the large number of EEG channels allow the use of more sophisticated methods of EOG artifact removal.

Several methods that differ in the way how brain and artifact activity are separated have been proposed. One known method is the Independent Component Analysis (ICA), which assumes, for example, that the summation of potentials arising from different parts of the brain, scalp, and body is linear at the electrodes. ICA-based artifact correction thus removes and separates artifacts by linear decomposition.

However, the great number of channels/electrodes needed render the methods used in brain research inappropriate for such clinical applications, in which the number of EEG signals/channels is to be kept, due to practical reasons, much lower, typically in one or two. In many clinical applications it is advantageous to place the EEG measurement electrodes only onto the forehead or other hairless areas of the patient's head, while artifact is removed by rejecting contaminated EEG epochs based on one or more EOG channels measured separately. Alternatively, artifact may be removed without the use of EOG channels based on the properties of the EEG signal itself, for example by rejecting epochs including excessive amplitudes of the signal. Rejected epochs may optionally be replaced by new data points derived from non-rejected data points by interpolation, for example.

A drawback of the EOG-based clinical methods is that efficient detection of the contaminated EEG epochs requires separate electrodes for recording the EOG signal(s). If no separate EOG electrodes are used in clinical applications, the artifact removal remains inefficient, since the omission of the EOG electrodes makes the knowledge about the presence of artifact unreliable. EOG is present and often visible in any facial electrode pair. These same electrode pairs also pick up low frequency brain activity. In order to obtain as independent information as possible about eye movements, dedicated electrodes are attached around the eyes. However, attaching the electrodes adds to the work of the nursing staff and causes inconvenience for the patient.

Movement of the electrodes relative to the skin is another potential source of artifacts. The relative movement may be caused by spontaneous head movements or head movements due to mechanical ventilation, for example. Vibration caused by the nursing staff walking close to the patient or accidentally rocking the patient bed may also couple to the electrode lead wires. Apart from the measurement of eye movements or blinks, other measurements of skin surface potential do not provide independent information about the existence of movement artifacts. Head movements can be monitored using, for example, an acceleration transducer. This method, however, has two drawbacks. First, it is not clear how the head movements and the EEG artifacts are related, because the amplitude of the possible EEG deflections depend on multiple variables, such as the quality of the electrode contact, the direction of the head movement, possible tension in the electrode lead wires, etc. Second, the method requires a dedicated acceleration transducer component either attached separately on the skin of the patient or integrated as part of one of the electrodes. This translates to additional cost and increased complexity of the system and its use.

Facial muscle activity causes high frequency (30-150 Hz) action potential signals (EMG) to superimpose on the EEG. In addition, the facial muscle activity causes low frequency components to the signal due to the movement of the electrodes relative to the skin. However, predicting low frequency EEG artifacts based on the high frequency signal content is not reliable, because muscle activity does not necessarily imply electrode movement and thus EEG artifact.

The present invention seeks to alleviate or eliminate the above-mentioned drawbacks and to accomplish an uncomplicated artifact detection mechanism suitable for clinical use.

SUMMARY OF THE INVENTION

The present invention seeks to provide a novel mechanism for detecting artifacts in a bioelectric signal, especially in a frontal EEG signal, thereby to enable elimination or suppression the artifacts appearing in the bioelectric signal to be analyzed or the effect of artifacts on an analysis performed based on the bioelectric signal. The present invention further seeks to provide a mechanism, which is suitable for use in a clinical environment, where the number of signal channels is normally low.

The present invention rests on the discovery that all the low-frequency interference sources hampering the analysis of an EEG signal measured from the facial area of the patient are such that they are reflected in an impedance signal measured from the same area. Therefore, bioimpedance and EEG signal data are measured simultaneously from the facial area of the patient, preferably from the forehead. Facial area here refers to the non-hairy area of the head from the chin to the top of the forehead, including mastoids.

Short-time variations in the impedance are monitored to detect the periods during which the EEG signal data is contaminated by artifact. The process may then discard either the corresponding EEG epochs or the analysis results calculated based on the contaminated data. Although the method is intended for EEG signals, it may be employed for any bioelectric signal for which a substantially simultaneous impedance signal acquired from a certain measurement area of the patient indicates the presence of artifact in the bioelectric signal.

As is discussed below, apart from the bioimpedance of the subject the impedance signal measured may also be indicative of the electrode-skin impedance thus possibly providing valuable information about the properties of the electrode contact.

Thus one aspect of the invention is providing a method for detecting artifact in a bioelectric signal. The method includes the steps of supplying an AC excitation signal through a signal path formed between two electrodes of a first electrode set attached to a subject's skin surface in a measurement area of the subject's body and measuring an impedance signal through a second electrode set attached to the subject's skin surface in the measurement area, the impedance signal being indicative of the impedance of the signal path. The method further includes the steps of acquiring a bioelectric signal through a third electrode set attached to the subject's skin surface in the measurement area, the acquiring step being performed simultaneously with the measuring step, determining at least one first time period during which the impedance signal fulfills at least one predetermined criterion, and defining, based on the at least one first time period, at least one artifact-contaminated time period of the bioelectric signal.

Another aspect of the invention is that of providing an apparatus for detecting artifact in a bioelectric signal. The apparatus includes signal generator means for supplying an AC excitation signal through a signal path formed between two electrodes of a first electrode set when said set is attached to a subject's skin surface in a measurement area of the subject's body and impedance measurement means for measuring an impedance signal indicative of the impedance of the signal path, the impedance measurement means comprising a second electrode set connectable to the measurement area. The apparatus further includes first biosignal measurement means for obtaining a bioelectric signal, the biosignal measurement means comprising a third electrode set connectable to the measurement area, first artifact detection means for determining at least one first time period during which the impedance signal fulfills at least one predetermined criterion, and second artifact detection means, responsive to the first artifact detection means, for defining at least one artifact-contaminated time period of the bioelectric signal.

The invention allows an uncomplicated mechanism for conveying information related to the electrode movement, facial muscle activity or eye movements, which are major artifact sources of a frontal EEG measurement. In one embodiment of the invention, the presence of artifact may be detected through the active EEG electrodes, i.e. no separate electrodes are needed for artifact detection.

A further aspect of the invention is that of providing a computer program product by means of which known measurement devices may be upgraded, provided that simultaneously measured and temporally aligned bioelectric and bioimpedance signal data are available. The program product includes a first program code portion configured to receive an impedance signal indicative of the impedance of a signal path between two electrodes attached to a subject's skin surface in a measurement area of the subject's body, a second program code portion configured to receive a bioelectric signal obtained through a set of electrodes attachable to the measurement area, a third program code portion configured to determine at least one first time period during which the impedance signal fulfills at least one predetermined criterion, and a fourth program code portion configured to define at least one artifact-contaminated time period of the bioelectric signal.

In one embodiment of the invention, short-time variations caused by eye blinks in the impedance are monitored to ascertain which of the artifact-contaminated time periods of the EEG signal data are caused by eye blinks. In this way, a highly specific eye blink detector may be constructed.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 8 in the appended drawings, wherein.

DETAILED DESCRIPTION OF THE INVENTION

As discussed above, the present invention rests on the discovery that the major low-frequency interference sources hampering the analysis of an EEG signal measured from the forehead of the patient are such that their presence may be identified from a bioimpedance signal measured from the forehead of the patient. Therefore, a simultaneous bioimpedance measurement indicates when an EEG signal is likely to be distorted by one or more of the said interference sources.

Bio-impedance measurement combined with biopotential measurement is applied in monitoring of the respiration of a patient, for example. U.S. Pat. No. 5,879,308 discloses a method for measuring bioimpedance in connection with an ECG measurement for monitoring the respiration and/or the blood circulation of the patient. In the bioimpedance measurement, an excitation signal is supplied from a signal generator to the active electrodes of the ECG measurement, whereby an impedance signal indicative of the impedance of the patient is obtained from the neutral electrode, which is connected to ground through a grounding impedance. The frequency of the excitation signal is well above the ECG signal band, typically at 30 kHz.

When applied to human facial areas, bioimpedance measurement provides information about blood flow, eye movements, and eye blinks, which affect the volume conduction properties. As discussed below, the bioimpedance measurement may also include information about changes in the electrode contacts, caused by either movement of the head or frowning.

Figure 1:
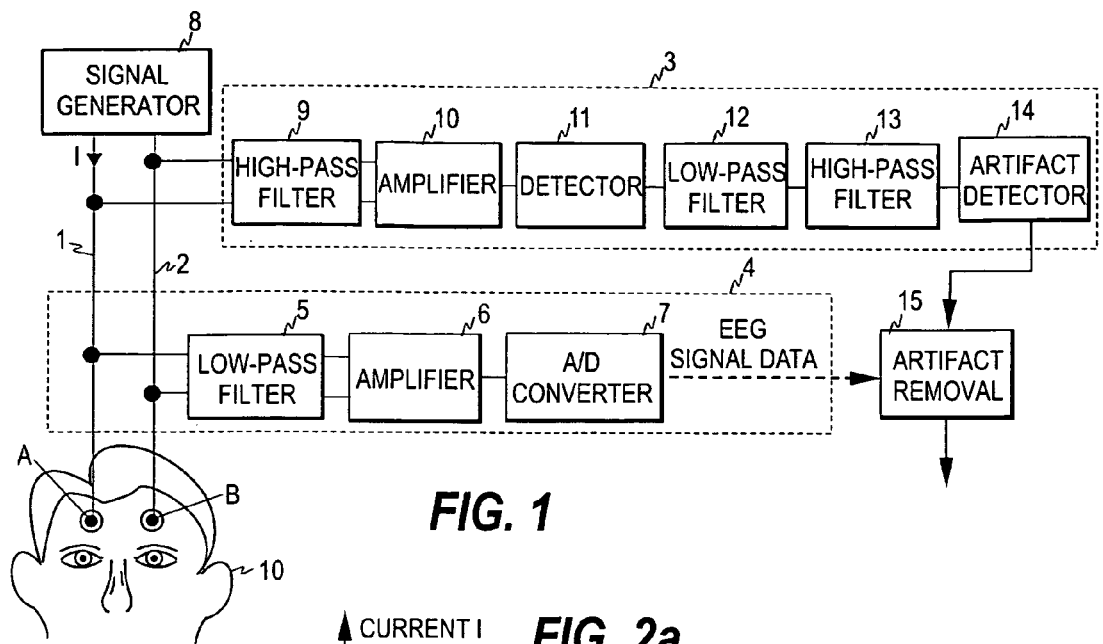
FIG. 1 illustrates one embodiment of the apparatus of the invention.

FIG. 1 illustrates one embodiment of the apparatus of the present invention, in which a 2-lead impedance measurement configuration is employed. Active electrodes A and B of an EEG measurement are attached in the facial area of a patient 10, preferably onto the forehead of the patient.

The EEG signal obtained from the electrodes is directed to an EEG measurement branch 4 comprising a low-pass filter 5 at its front end.

Figure 2A:
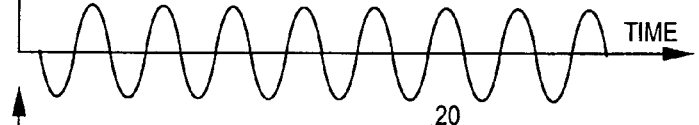
FIG. 2a illustrates the AC excitation signal supplied to the patient in the embodiment of FIG. 1.

In the 2-lead configuration, the excitation signal of the bioimpedance measurement is fed to the same electrodes from where the EEG signal is acquired. For supplying the excitation signal, the apparatus includes a signal generator 8 connected to electrodes A and B through corresponding wires 1 and 2. The frequency of the excitation signal supplied to the patient is well above the EEG signal band, typically in the range of 20-100 kHz, in order to enable continuous and simultaneous bioimpedance measurement that does not interfere with the EEG measurement. FIG. 2a illustrates the excitation signal output from the signal generator.

The impedance signal is measured from the same electrodes by connecting an impedance measurement branch 3 to wires 1 and 2. The impedance measurement branch includes a high-pass filter 9 at its front end.

The low-pass filter 5 of the EEG measurement branch prevents high frequencies, i.e. the excitation signal, from entering the EEG measurement branch, while the high-pass filter 9 prevents the low frequencies, i.e. the EEG signal, from entering the impedance measurement branch.

In the measurement branches the filtered signals are first amplified; the EEG signal is supplied to an amplifier 6 of the EEG measurement branch, while the impedance signal is supplied to an amplifier 10 of the impedance measurement branch. The amplifiers are typically differential amplifiers.

The EEG measurement branch further includes an A/D converter 7 that samples the EEG signal and converts it into digitized format. The A/D converter thus outputs a sequence of EEG signal data. After the low-pass filter 5, the EEG signal is processed in a conventional manner to obtain the said sequence. As is common in the art, the digitized signal samples are processed as sets of sequential signal samples representing finite time blocks or time windows, commonly termed "epochs".

Figure 2B:
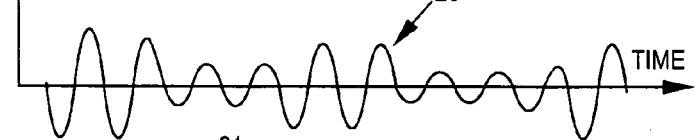
FIG. 2b to 2d illustrate the measured impedance signal in different points of the impedance measurement branch of the apparatus of FIG. 1.

In the 2-lead configuration, the signal generator supplies an excitation current I to the patient. The voltage between the electrodes, i.e. the signal measured by the impedance measurement branch, is then proportional to the impedance of the signal path formed between electrodes A and B. At this stage, the frequency content of the measured signal is concentrated around the frequency of the excitation current. FIG. 2b illustrates the impedance signal 20 output from amplifier 10. As can be seen, impedance changes cause slow changes in the signal.

Figure 2C:
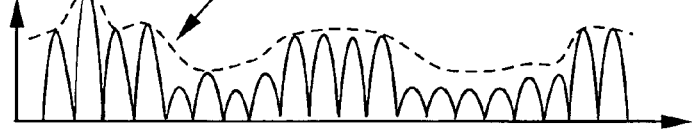

In order to analyze the impedance changes over time, the impedance signal is typically demodulated in a detector 11 using the excitation frequency. This produces a time-varying signal indicating how the impedance of the signal path varies over time. As is shown in FIG. 2c, the detector typically outputs an impedance signal 21, which corresponds to the envelope of the rectified input signal 20 and varies slowly over time in accordance with the impedance changes. This signal is then typically low-pass filtered in a first filter 12 in order to reduce noise, and further high-pass filtered in a second filter 13 to remove the often uninteresting DC component and low-frequency fluctuation.

Figure 2D:
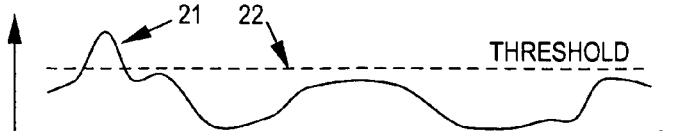

The filtered impedance signal is then supplied to an artifact detector 14, which may compare the impedance signal 21 with a predetermined threshold 22, as is illustrated in FIG. 2d, and determine the time periods during which the impedance signal exceeds the threshold. These periods are regarded as contaminated by artifact and the temporal location of the periods is utilized to eliminate or suppress the effect of the artifact on the EEG analysis. This is performed in an artifact removal unit 15. As noted above, the DC value of the impedance signal is typically removed, in which case the alternating component of the impedance is compared with the threshold.

It is also possible to use an excitation frequency, which is at or close to the EEG frequency band. In this case both the EEG signal and the impedance signal may be amplified and digitized as one composite signal and the rest of the above-described steps may be implemented as software algorithms.

As noted above, the bioimpedance measurement provides information about blood flow and thus includes a periodic component at a frequency corresponding to the pulse rate of the patient. Since the said component represents artifact from the point of view of the detection of eye movements and blinks, the said pulsating component may be removed from the impedance signal in one embodiment of the invention. This may be performed in high-pass filter 13 or in a separate removal unit before or after the high-pass filter, for example.

Figure 3:
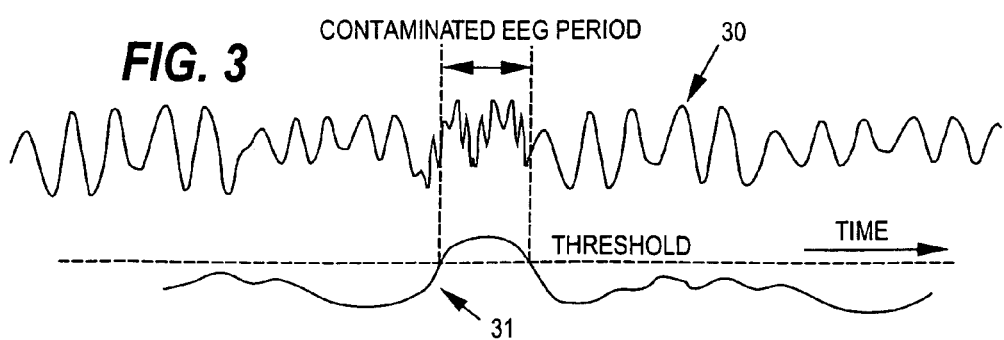
FIG. 3 illustrates the detection of the contaminated EEG periods.

FIG. 3 illustrates the above-described detection of the contaminated EEG periods by showing a segment of an EEG signal 30 and a segment of an impedance signal 31. Since the two signals are simultaneously measured and thus temporally aligned, the periods during which the bioimpedance exceeds a predetermined threshold directly indicate the contaminated periods of the EEG signal. The corresponding data points in the EEG data sequence may then be flagged to indicate that the said data is not reliable.

Figure 4:
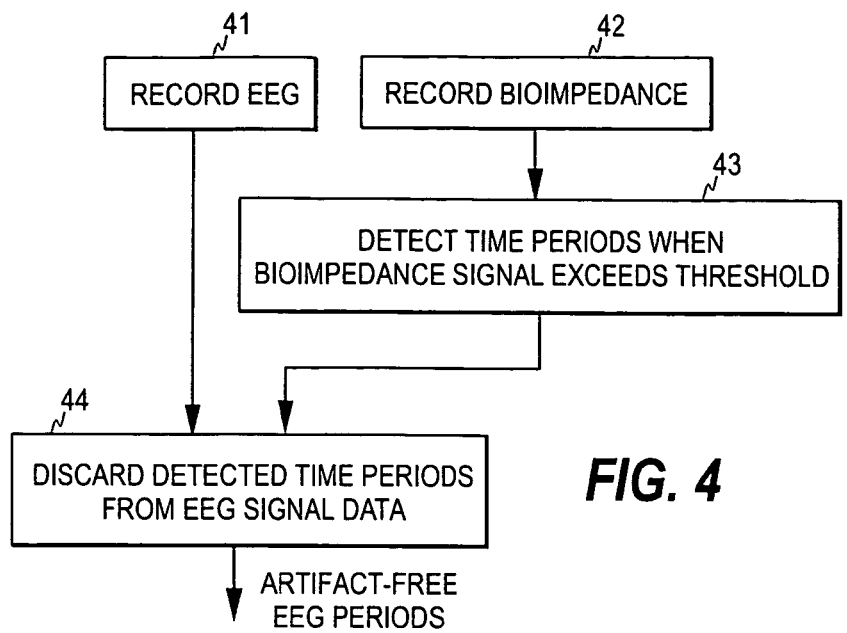
FIG. 4 is a flow diagram illustrating one embodiment of the method of the invention.

FIG. 4 illustrates one embodiment of the method of the invention. As noted above, an EEG signal and a bioimpedance of the patient are measured simultaneously from the forehead of the patient (steps 41 and 42). The bioimpedance signal is continuously monitored and the time periods are determined during which the bioimpedance signal exceeds a predetermined threshold level (step 43). Based on the determined periods, the EEG signal data is then defined, which corresponds to the determined periods, and the said data is discarded from the sequence of the EEG signal data (step 44). In this embodiment, the resulting EEG sequence output from the artifact removal unit 15 thus includes only data that corresponds to artifact-free periods of the measurement. The EEG analysis may then be performed based on the said artifact-free data. Optionally, the discarded data may be replaced by interpolating new data values from non-rejected data points or by filling the gaps with zeroes, for example.

Figure 5:
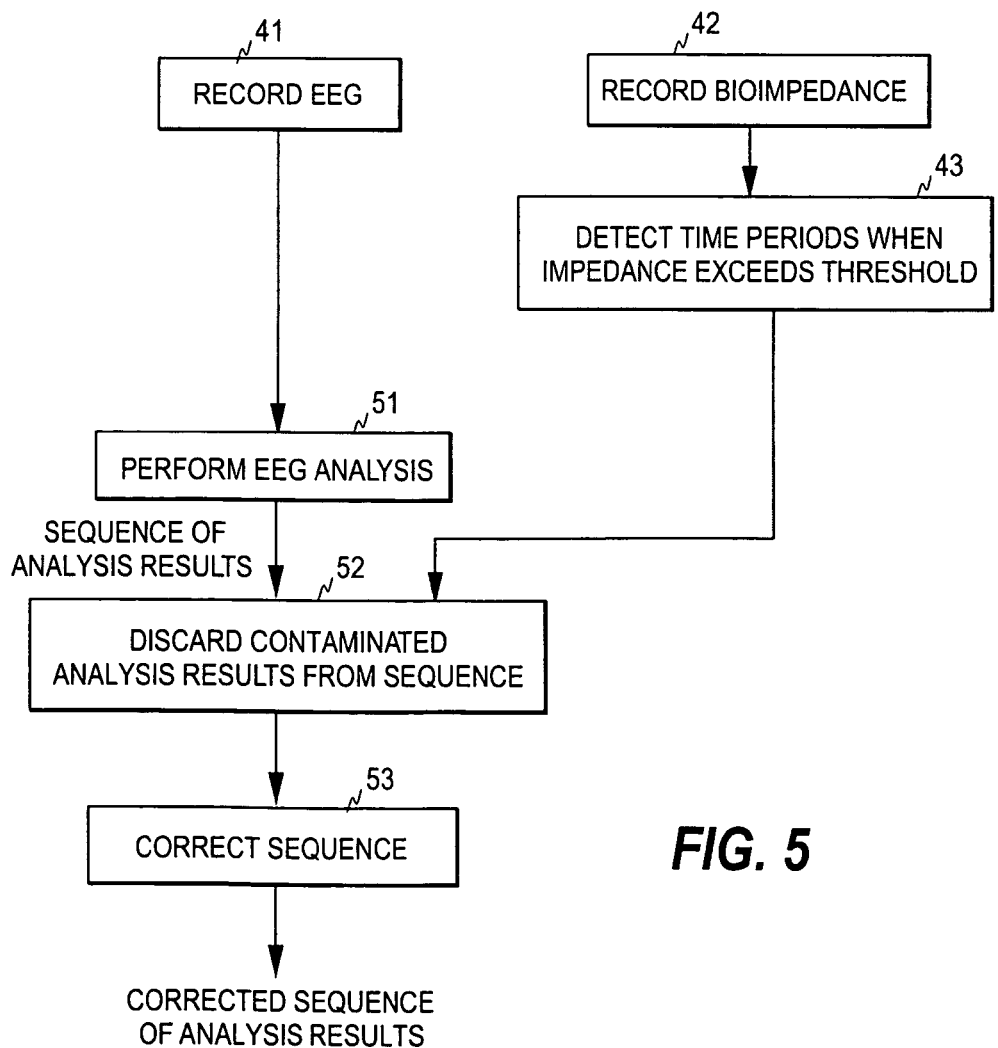
FIG. 5 is a flow diagram illustrating another embodiment of the method of the invention.

FIG. 5 illustrates another embodiment of the method of the invention. In this embodiment, the initial steps correspond to steps 41 to 43 of the embodiment of FIG. 2. However, the time periods determined at step 43 are not used to discard EEG signal data, but the EEG analysis is first performed based on the EEG signal data containing contaminated periods (step 51). As a result, a sequence of analysis results is obtained. Based on the periods determined at step 43, the analysis results that correspond to the contaminated periods are rejected from the sequence (step 52). As the resulting sequence then includes gaps, new values may then be interpolated to fill the gaps (step 53), whereby a corrected sequence of analysis results is obtained. The EEG analysis may involve any known analysis method. In an entropy-based analysis, for example, a sequence of entropy values is obtained. The interpolation of new values may also be omitted. In this case the graphically presented EEG signal thus includes gaps.

Above, the time periods are determined during which the bioimpedance signal exceeds a predetermined threshold level and the EEG signal data or the analysis results are rejected, which correspond to the said time periods. However, the measurement may also be carried out so that the time periods are determined during which the impedance signal is undisturbed (i.e. remains below the predetermined threshold level), while the remaining time periods are regarded as contaminated by artifact.

In the 2-lead configuration, the impedance signal is sensitive to changes both in the volume conductor and in the electrode contacts, i.e. to changes both in the impedance of the volume conductor (bioimpedance) and in the electrode-skin impedances. The effect of the electrode contacts on the impedance signal may be removed, and thus the specificity of the measurement improved, by using a 4-lead measurement configuration illustrated in FIG. 6. In this embodiment, four electrodes A to D are attached onto the forehead of the patient, the electrodes being preferably in the same line. The excitation current is supplied to the electrodes A and B, and the voltage, i.e. the impedance signal, is measured from the electrodes C and D.

Figure 6:
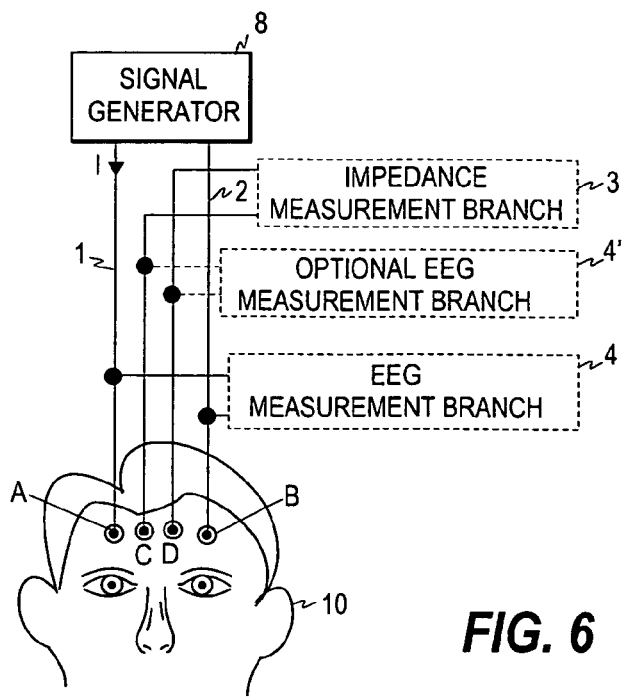
FIG. 6 illustrates an embodiment of the apparatus employing four measurement electrodes.

In the 4-lead measurement configuration the EEG measurement branch 4 may be linked either with the excitation branch comprising electrodes A and B, or with the impedance measurement branch comprising electrodes C and D. Furthermore, it is possible to record EEG from both electrode pairs simultaneously using two EEG measurement branches. FIG. 6 illustrates these alternatives by showing a primary EEG measurement branch 4 connected to electrodes A and B and an optional EEG measurement branch 4' connected to electrodes C and D. As noted above, the primary EEG measurement branch may also be connected to electrodes C and D and the optional EEG measurement branch to electrodes A and B.

Although the 4-lead measurement configuration improves the specificity of the measurement, the information about the properties of the electrode contacts may also be essential in view of artifact detection.

Figure 7:
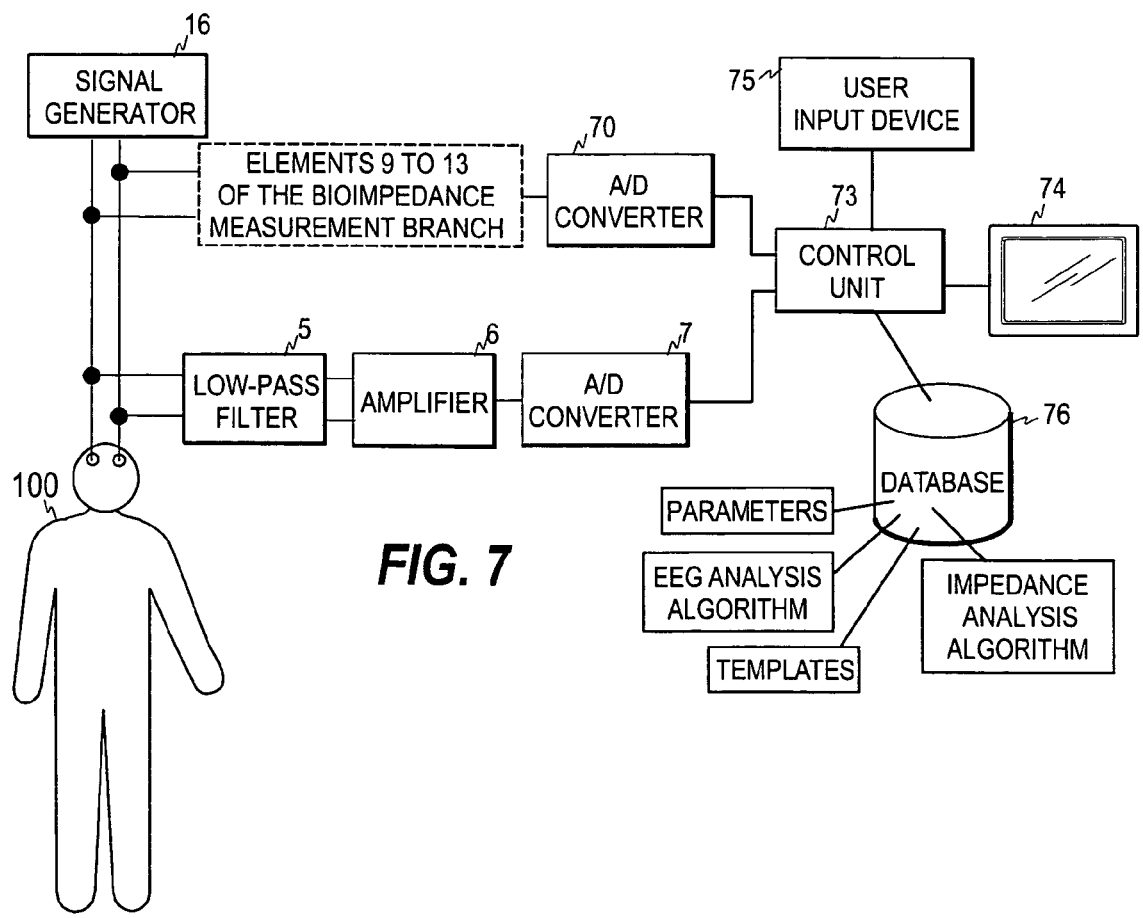
FIG. 7 illustrates one embodiment of the system of the invention.

FIG. 7 illustrates one embodiment of the system or apparatus according to the invention. Similar elements have been provided with the same reference numbers as above, and elements 9 to 13 of FIG. 1 are denoted with one block. In this embodiment, the digitized EEG signal data is supplied to a control unit 73 which may comprise one or more computer units or processors. The impedance signal output from high-pass filter 13 is converted into digitized format in an A/D converter 70, which supplies the digitized impedance signal to the control unit. In this embodiment, the control unit thus takes over the role of the artifact detector 14 and the artifact removal unit 15 of FIG. 1. In other words, the control unit compares the impedance signal with the predetermined threshold, detects the contaminated periods in the EEG signal data, and discards the contaminated EEG epochs or the contaminated analysis results. The control unit may also remove the above-described periodic component from the impedance signal prior to the comparison of the impedance signal with the predetermined threshold.

The control unit is provided with a memory or database 76 holding the digitized EEG data and the digitized impedance data. The memory or database may also store the algorithm for analyzing the impedance data, various parameters needed in the artifact detection, such as the threshold value with which the impedance signal is compared, and the EEG analysis algorithm. The control unit may further correct the analysis result sequence by filling the gaps caused by the artifact removal.

The signals, the contaminated signal periods, and/or the analysis results may be displayed on the screen of a monitor 74, which forms part of the user interface of the apparatus/system. As discussed above, the result sequence may be gapped or flagged to indicate when the results are not reliable.

Although a control unit comprising one computer unit or one processor may perform the above steps, the processing of the data may also be distributed among different units/processors (servers) within a network, such as a hospital LAN (local area network). The apparatus of the invention may thus also be implemented as a distributed system.

The user may control the operation of the apparatus/system through a user input device 75, such as a keyboard.

A patient monitor in which EEG and continuous bioimpedance data are available may also be upgraded to enable the monitor to remove contaminated data or analysis results. Such an upgrade may be implemented by delivering to the patient monitor a software module that enables the device to detect and eliminate artifact in the above-described manner. The software module may be delivered, for example, on a data carrier, such as a CD or a memory card. The software module may be provided with interfaces for receiving EEG and impedance data. The software module then performs, utilizing the impedance data available, the above-described artifact detection and outputs an artifact-free EEG data sequence or analysis result sequence. The software module may receive the EEG and bioimpedance signals in real-time directly from the electrodes of the monitor or from the memory of the patient monitor after the actual measurement. In the latter case, the signals may already be temporally aligned by time stamps attached to the signal values.

In the above examples, the detection of artifact is based on a comparison of the bioimpedance signal with a predetermined threshold. However, the detection may also be based on a software algorithm that searches for certain type deflections in the bioimpedance signal, i.e. deflections with a certain morphology. For example, eye blinks and movements of the eye balls may be distinguished from each other based on the morphologies of the deflections they cause. As a result, different type of artifacts may be processed in different ways. One appropriate method for detecting artifacts is to calculate signal power from predefined, consecutive or overlapping (of the order of 1 second) time windows of the impedance signal and to compare the power level of the window either with a fixed or an adaptive power threshold. Alternatively, the detection process may calculate the correlation between a predefined morphology (i.e. a template) and the impedance signal within each time window, and compare the correlation with a predetermined correlation threshold. In the apparatus/system of FIG. 7, these steps may be carried out in the control unit. Thus, in one embodiment the control unit divides the impedance signal into a series of time windows, calculates the power of the impedance signal in each time window, and compares the power of each time window with the power threshold. Artifact is detected if the calculated power exceeds the threshold. In another embodiment, the control unit divides the impedance signal into a series of time windows, calculates the correlation between a predetermined morphology and the impedance signal within each time window, and compares the correlation of each time window with the correlation threshold. Artifact is again detected if the calculated correlation exceeds the threshold.

Figure 8:
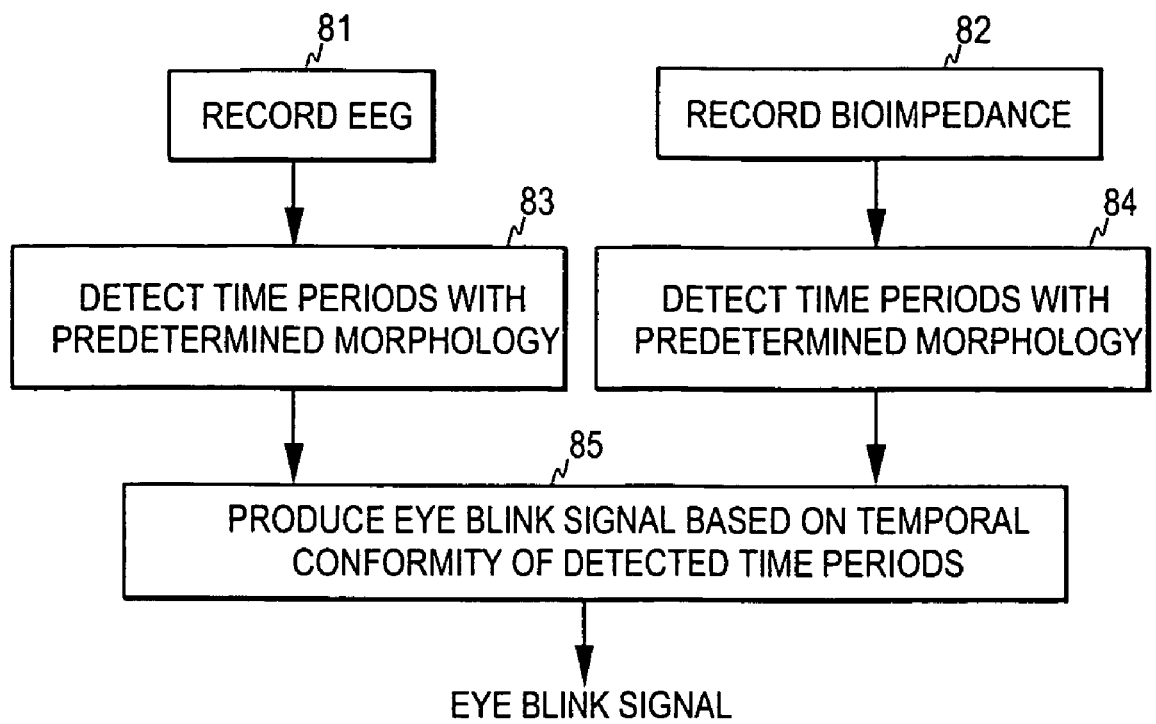
FIG. 8 is a flow diagram illustrating a further embodiment of the invention.

FIG. 8 illustrates an embodiment in which the mechanism of the invention is used to detect which of the artifact-contaminated time periods of the EEG signal data are caused by eye blinks.

The EEG and bioimpedance signals of the patient are again measured simultaneously from the forehead of the patient (steps 81 and 82). However, in this embodiment the bioimpedance signal is not compared with a predetermined threshold level, since the purpose is to detect only the artifacts caused by eye blinks. In this case, the bioimpendance signal is compared with a predefined morphology, i.e. a template, to detect the periods that include certain type of deflections, i.e. deflections caused by eye blinks (step 84).

The same detection mechanism is applied to the EEG signal at step 83. However, the template used for the EEG signal is different from the one used for the bioimpedance signal, since the deflections caused by eye blinks have different characteristics in the two signals.

Based on the temporal conformity of the eye blink originated deflections detected in the two signals, an eye blink signal is then produced, which indicates the eye blinks of the patient (step 85). More particularly, if the deflections detected by the templates are temporally close to each other, i.e. if a deflection detected in one of the signals has a corresponding deflection in the other signal and the said two deflections fit into a short time window, the process decides that the said time window includes an eye blink.

Thus, in this embodiment, different criteria are used to identify the artifact contaminated time periods in the bioimpedance signal, since only the artifacts caused by eye blinks are of interest. Blinks are detected independently for the bioimpedance and EEG signals and out of all detected deflections the ones are accepted, which occur substantially at the same time in both signals. Steps 83 to 85 may be carried out in the control unit.

Instead of template matching, a wavelet analysis may be employed in steps 83 and/or 84 to detect the deflections caused by eye blinks.

A highly specific blink detector may be constructed in the above manner. The reason for the high specificity is the relative independence of the two signals. EEG reflects changes in the electric potential distribution, which is affected by the electrical activity of the brain, changes of the dipolar electric field of the eyeball, and changes in the electrode-skin contact potential. Impedance, in turn, is sensitive to the mechanical movement of the electrodes and to the geometric changes in the volume conductor formed by the forehead. Closing of the eyelid translates to a significant change in the volume conductor geometry. This affects both the electric field of the eyeball and the impedance measured from the vicinity of the eye. Consequently, the temporal behavior of the two signals is very similar in this respect. Generally, the two signals are sensitive to different phenomena, but behave similarly in this respect.

The existence of blinks indicates that the eyes are open, i.e. the eye blink signal indicates when the eyes are open. This in turn provides useful information about the status of the patient. In sleep stage scoring of healthy subjects an "eyes open" state can usually be associated with awake state. In case of intensive care patients, the existence of sleep-like EEG patterns while the eyes are open may point to an abnormal state of the brain. Thus, even though the deflections searched for are artifacts in regard to the EEG analysis, the resulting blink signal is a useful signal in patient monitoring.

Although the invention was described above with reference to the examples shown in the appended drawings, it is obvious that the invention is not limited to these, but may be modified by those skilled in the art without departing from the scope of the invention. For example, the impedance signal may be measured in various ways. As a result, the relationship between the impedance signal and the actual impedance may also vary. Therefore, the predetermined criterion/criteria indicating the presence of artifact may also vary. In some embodiments, for example, an impedance signal exceeding a predetermined threshold may indicate the absence of artifact.

The invention claimed is:

1. A method for detecting artifacts in a bioelectric signal, the method comprising the steps of:
   supplying an AC excitation signal through a signal path formed between a first electrode and a second electrode each attached to a subject's skin surface in a measurement area of the subject's body, the AC excitation signal having a frequency above a signal band including the bioelectric signal;
   measuring an impedance signal through the first and second attached to the subject's skin surface in the measurement area, the impedance signal being indicative of the impedance of the signal path;
   acquiring the bioelectric signal through the first and second attached to the subject's skin surface in the measurement area, the acquiring step being performed simultaneously with the measuring step;
   determining at least one first time period during which the impedance signal fulfills at least one predetermined criterion using a control unit; and
   based on the at least one first time period, defining at least one artifact-contaminated time period of the bioelectric signal using the control unit.

2. A method according to claim 1, wherein the acquiring step includes acquiring the bioelectric signal, in which the bioelectric signal is an EEG signal.

3. A method according to claim 2, wherein the supplying step includes supplying the AC excitation signal through the signal path formed between the first and second electrodes attached to the subject's skin surface in the measurement area of the subject's body, in which the measurement area comprises the facial area of the subject.

4. A method according to claim 2, wherein the supplying step includes supplying the AC excitation signal through the signal path formed between the first and second electrodes attached to the subject's skin surface in the measurement area of the subject's body, in which the measurement area comprises the forehead of the subject.

5. A method according to claim 1, further comprising a step of discarding signal segments in the bioelectric signal that correspond to the at least one artifact-contaminated time period from the bioelectric signal.

6. A method according to claim 5, further comprising a step of replacing the discarded signal segments of the bioelectric signal with new signal values.

7. A method according to claim 1, further comprising the steps of:
analyzing the bioelectric signal, whereby a sequence of analysis results is obtained; and
discarding analysis results that correspond to the at least one artifact-contaminated time period from the sequence of analysis results.

8. A method according to claim 7, further comprising a step of replacing the discarded analysis results with new analysis values.

9. A method according to claim 1, wherein
the measuring step further includes a sub-step of connecting the first and second electrodes to a high-pass filter configured to pass signals on a frequency range of the AC excitation signal and reject signals on a frequency range of the bioelectric signal; and
the acquiring step includes a sub-step of connecting the first and second electrodes to a low-pass filler configured to reject signals on a frequency range of the AC excitation signal and pass signals on a frequency range of the bioelectric signal.

10. A method according to claim 1, further comprising a step of removing a periodic signal component from the impedance signal, the periodic signal component being caused by pulsating blood flow in the measurement area.

11. A method according to claim 1, wherein the determining step includes comparing the amplitude of the impedance signal with a predetermined threshold value.

12. A method according to claim 1, wherein the determining step includes the sub-steps of
dividing the impedance signal into a series of time windows;
determining the power of the impedance signal in each time window; and
comparing the power in each time window with a power threshold.

13. A method according to claim 1, wherein the determining step includes the sub-steps of
dividing the impedance signal into a series of time windows;
determining the correlation between a predetermined signal morphology and the impedance signal within each time window; and
comparing the correlation of each time window with a predetermined correlation threshold.

14. A method according to claim 1, wherein the defining step includes the sub-steps of
defining at least one second time period during which the bioelectric signal fulfills at least one second predetermined criterion; and
determining time windows during which the at least one first time period and the at least one second time period meet a predetermined concurrence criterion,
wherein the time windows represent the at least one artifact-contaminated time period.

15. A method according to claim 14, wherein the determining step and the defining sub-step include template matching.

16. A method according to claim 14, wherein the determining step and the defining sub-step include performing a wavelet analysis.

17. A method according to claim 1, wherein the frequency of the AC excitation signal is between 20-100 kHz.

18. An apparatus for detecting artifacts in a bioelectric signal, the apparatus comprising:
signal generator means for supplying an AC excitation signal through a signal path formed between a first electrode and a second electrode when said first and second electrodes are attached to a subject's skin surface in a measurement area of the subject's body, the AC excitation signal having a frequency above a signal band including the bioelectric signal;
impedance measurement means for measuring an impedance signal indicative of the impedance of the signal path, the impedance measurement means comprising the first and second electrodes connectable to the measurement area;
first biosignal measurement means for obtaining a bioelectric signal, the biosignal measurement means comprising the first and second electrodes connectable to the measurement area;
first artifact detection means for determining at least one first time period during which the impedance signal fulfills at least one predetermined criterion; and
second artifact detection means, responsive to the first artifact detection means, for defining at least one artifact-contaminated time period of the bioelectric signal.

19. An apparatus according to claim 18, wherein the first biosignal measurement means are configured to obtain an EEG signal from the subject.

20. An apparatus according to claim 19, wherein the measurement area comprises at least part of the facial area of the subject.

21. An apparatus according to claim 18, further comprising means for discarding signal segments in the bioelectric signal that correspond to the at least one artifact-contaminated time period from the bioelectric signal.

22. An apparatus according to claim 21, further comprising means for replacing the discarded signal segments of the bioelectric signal with new signal values.

23. An apparatus according to claim 18, further comprising
means for analysing the bioelectric signal, whereby a sequence of analysis results is obtained; and
means for discarding analysis results that correspond to the at least one artifact-contaminated time period from the sequence of analysis results.

24. An apparatus according to claim 23, further comprising means for replacing the discarded analysis results with new analysis values.

25. An apparatus according to claim 18, wherein the first and second electrodes are connected to a high-pass filter configured to pass signals on a frequency range of the AC excitation signal and reject signals on a frequency range of the bioelectric signal and the first and second electrodes are connected to a low-pass filter configured to reject signals on a frequency range of the excitation signal and pass signals on a frequency range of the bioelectric signal.

26. An apparatus according to claim 18, wherein the impedance measurement means comprise means for removing a pulsating signal component from the impedance signal, the pulsating signal component being caused by pulsating blood flow in the measurement area.

27. An apparatus according to claim 18, wherein the first artifact detection means are configured to compare the amplitude of the impedance signal with a predetermined threshold value.

28. An apparatus according to claim 18, wherein the first artifact detection means are configured to divide the impedance signal into a series of time windows, determine the power of the impedance signal in each time window, and compare the power of each time window with a power threshold.

29. An apparatus according to claim 18, wherein the first artifact detection means are configured to divide the impedance signal into a series of time windows, determine the correlation between a predetermined signal morphology and the impedance signal within each time window, and compare the correlation of each time window with a predetermined correlation threshold.

30. An apparatus according to claim 18, wherein the second artifact detection means are configured to
define at least one second time period during which the bioelectric signal fulfills at least one second predetermined criterion; and
determine time windows during which the at least one first time period and the at least one second time period meet a predetermined concurrence criterion,
wherein the time windows represent the at least one artifact-contaminated time period.

31. An apparatus according to claim 30, wherein at least one of the first artifact detection means and the second artifact detection means is configured to employ template matching in determining the at least one first time period and in defining the at least one second time period, respectively.

32. An apparatus according to claim 30, wherein at least one of the first artifact detection means and the second artifact detection means is configured to employ wavelet analysis in determining the at least one first time period and in defining the at least one second time period, respectively.

33. An apparatus for detecting artifacts in a bioelectric signal, the apparatus comprising:
a signal generator configured to supply an AC excitation signal through a signal path formed between a first electrode and a second electrode when the first and second electrodes are attached to a subject's skin surface in a measurement area of the subject's body, the AC excitation signal having a frequency above a signal band including the bioelectric signal;
a first measurement branch operatively connected to the first and second electrodes, the first measurement branch being configured to measure an impedance signal indicative of the impedance of the signal path;
a second measurement branch operatively connected to the first and second electrodes, the second measurement branch being configured to measure a bioelectric signal from the subject;
a first controller configured to determine at least one first time period during which the impedance signal fulfills at least one predetermined criterion; and
a second controller, responsive to the first controller, configured to define at least one artifact-contaminated time period of the bioelectric signal.

34. An apparatus according to claim 33, wherein
the first measurement branch comprises a first filter configured to pass signals on a frequency range of the AC excitation signal and reject signals on a frequency range of the bioelectric signal; and
the second measurement branch comprises a second filter configured to reject signals on a frequency range of the excitation signal and pass signals on a frequency range of the bioelectric signal.

35. A computer program product stored on a computer readable medium and operable for detecting artifacts in a bioelectric signal, the computer program product comprising:
a first program code portion configured to receive an impedance signal indicative of the impedance of a signal path between first and second electrodes attached to a subject's skin surface in a measurement area of the subject's body;
a second program code portion configured to receive a bioelectric signal obtained through the first and second electrodes attachable to the measurement area;
a third program code portion configured to determine at least one first time period during which the impedance signal fulfills at least one predetermined criterion; and
a fourth program code portion configured to define at least one artifact-contaminated time period of the bioelectric signal.

36. A method for detecting artifacts in an EEG signal, the method comprising the steps of:
supplying an AC excitation signal through a signal path formed between a first electrode and a second electrode each attached to a subject's skin surface in a measurement area of the subject's body, the AC excitation signal having a frequency above an EEG signal band;
measuring an impedance signal through the first and second electrodes, the impedance signal being indicative of the impedance of the signal path;
acquiring the EEG signal through the first and second electrodes, the acquiring step being performed simultaneously with the measuring step;
determining at least one first time period during which the impedance signal fulfills at least one predetermined criterion using a control unit; and
based on the at least one first time period, defining at least one artifact-contaminated time period of the EEG signal using the control unit.

37. The method of claim 36 wherein the frequency of the AC excitation signal is between 20-100 kHz.

* * * * *